United States Patent

Ahmad et al.

Patent Number: 5,114,580
Date of Patent: May 19, 1992

[54] COMBINED HEMOFILTRATION AND HEMODIALYSIS SYSTEM

[75] Inventors: Suhail Ahmad, Seattle; James J. Cole, Arlington; William Jensen, Seattle, all of Wash.

[73] Assignee: The Board of Regents of the University of Washington, Seattle, Wash.

[21] Appl. No.: 540,747

[22] Filed: Jun. 20, 1990

Related U.S. Application Data

[63] Continuation-in-part of Ser. No. 368,665, Jun. 20, 1989, abandoned.

[51] Int. Cl.⁵ ............... B01D 61/28; B01D 61/32; B01D 61/34
[52] U.S. Cl. .................. 210/646; 210/651; 210/739; 210/805; 210/806; 210/143; 210/188; 210/195.2; 210/196; 210/257.2; 210/295; 210/371.6; 210/321.65; 210/321.72; 210/416.1; 210/417; 210/929; 417/20; 417/471
[58] Field of Search ............ 210/85, 86, 94, 98, 210/103, 143, 188, 195.2, 205, 206, 257.2, 321.65, 321.71–321.9, 416.1–416.5, 417, 929, 646, 651, 739, 805, 806, 137, 321.6; 604/4–6, 250–255; 417/20, 470–475

[56] References Cited

U.S. PATENT DOCUMENTS

| | | | |
|---|---|---|---|
| 3,579,441 | 5/1971 | Brown | 210/641 |
| 3,902,490 | 9/1975 | Jacobsen et al. | 210/990 X |
| 4,500,309 | 2/1985 | Diederich et al. | 604/5 |
| 4,514,295 | 4/1985 | Mathieu et al. | 604/5 |
| 4,596,550 | 6/1986 | Troutner | 604/5 |
| 4,601,712 | 7/1986 | Cole et al. | 604/251 |
| 4,650,458 | 3/1987 | Dahlberg et al. | 604/5 |
| 4,676,905 | 6/1987 | Nagao et al. | 210/416.1 |
| 4,702,829 | 10/1987 | Polaschegg | 210/321.72 |
| 4,857,199 | 8/1989 | Cortial | 210/321.65 |
| 4,885,001 | 12/1989 | Leppert | 604/4 |
| 4,897,189 | 1/1990 | Greenwood et al. | 210/416.1 |

Primary Examiner—W. Gary Jones
Attorney, Agent, or Firm—Seed and Berry

[57] ABSTRACT

A hemodialysis system has a blood circuit and a hemofiltrate circuit interconnected at a hemofilter and an air collection chamber. If an infusion of sterile fluid to the returning blood is needed during the dialysis treatment, filtrate in the filtrate circuit is pumped back into the blood circuit. This is also done to purge the blood circuit of blood and return it to the patient at the conclusiion of a dialysis treatment. A blood pump in the blood circuit incorporates a flexible vessel in conjunction with pinch valves which self expand in a controlled manner from a compressed condition to fill with blood from the patient in a suction stroke controlled by the patient's blood delivery rate. Compression of the vessel by an external member then forces the blood through the rest of the blood circuit.

28 Claims, 2 Drawing Sheets

COMBINED HEMOFILTRATION AND HEMODIALYSIS SYSTEM

CROSS REFERENCE TO RELATED APPLICATION

This application is a continuation-in-part of our copending application Ser. No. 368,665, filed Jun. 20, 1989, entitled "Automated Hemodialysis System," now abandoned.

TECHNICAL FIELD

The present invention relates to hemodialysis systems, and more particularly, to an improved such system having blood and hemofiltrate circuits interconnected at a hemofilter and an air collection chamber, and having a novel blood pump operating according to the patient's blood delivery rate.

BACKGROUND OF THE INVENTION

Hemodialysis treatment is employed as a therapeutic measure when a patient's kidneys no longer perform their blood purifying function because of disease or traumatic removal. Kidney failure results in the accumulation of toxic waste in the patient's blood and eventual death from uremic poisoning, unless the waste material is removed by some artificial means. In hemodialysis of the type to which the present invention relates, the patient's blood is circulated from the patient in a closed blood circuit by a pump to one side of a membrane contained within a hemodialyzer (i.e., artificial kidney). The membrane has pores of microscopic size through which waste products from the blood pass. The pores are, however, too small to permit blood cells and proteins to leave the body. A dialysis fluid (dialysate) is circulated on the other side of the hemodialyzer membrane to remove the waste products. The dialyzed blood is returned to the patient.

The blood pump normally used in contemporary dialysis systems is a roller pump in which rollers on rotating arms radiating from a motor-driven shaft progressively squeeze closed a section of flexible tubing in the circuit connecting the patient's blood system to the hemodialyzer. The speed of the pump motor is set to give a pump output in accordance with the anticipated patient's blood delivery rate. However, this delivery rate will normally vary during treatment and may drop below the pump output setting, a condition likely to collapse and obstruct the connection tubing. In contemporary dialysis machines an alarm is triggered and the blood pump is stopped if the patient's blood delivery rate drops below the pump flow rate setting. To minimize the occurrence of such a condition the blood pump is normally given a flow rate setting below the anticipated blood flow rate from the patient to allow for downward fluctuations of the patient's blood delivery rate. Hence, the treatment time is longer than would be necessary if the pumping rate continuously matched the patient's blood delivery rate.

SUMMARY OF THE INVENTION

The present invention regulates the blood flow rate through the blood circuit of the dialysis system according to the available blood delivery rate from the patient, thereby avoiding recurring alarms and reducing staffing needs. In some instances, optimization of blood flow may also shorten dialysis treatment time. Regulation by the blood delivery rate of the patient is accomplished in the practice of the present invention by providing a blood pump having a compressible pump chamber and having flexible ingress and egress tubes at opposite ends of the chamber which extend through pinching devices functioning together with the tubes as ingress and egress pinch valves. The pump chamber walls are sufficiently elastic to self return the pump chamber to its normal size from a compressed condition when compression is released.

Expansion of the pump chamber toward its normal size from a compressed empty condition creates a suction which aids in filling the chamber with blood from the patient. When filling of the pump chamber is complete the ingress valve closes and the egress valve opens. Then compression of the pump chamber commences for delivery of blood from the chamber to the rest of the dialysis system during a compression stroke. At the close of the chamber compression stroke the compression device commences a chamber expansion stroke with the egress valve closed and the ingress valve open. During this chamber expansion stroke the compressing device remains in engagement with a wall of the pump chamber, and the chamber expansion stroke is permitted to advance only at a pace determined by the blood delivery rate from the patient as it then exists.

In contemporary dialysis systems usually the tubing is replaced after each treatment. This is always done in dialysis treatment centers in which multiple patients use the same dialysis machine. The time and expense involved in tubing replacement is significant. The present invention makes it possible to backwash the tubing and other components of the dialysis system so as to make it possible to reuse the system with the tubing remaining in place on the machine for several treatments in situations such as home dialysis in which the dialysis machine is only used by one patient. The present invention also makes it possible in installations in which a dialysis machine is used for treating multiple patients in sequence to remove the tubing and system elements to which the tubing is connected as a module for reuse for the same patient.

Occasionally a patient will experience discomfort or shock symptoms. In the past such occurrences have been remedied by an infusion of a sterile solution from an external source to the returning blood. The present invention provides a filtrate circuit integrated in a closed system with the blood circuit in the dialysis machine in such a manner that some of the filtrate can readily be pumped back into the blood circuit and returned to the patient rather than supplementing with fluids from an external source.

DETAILED DESCRIPTION OF THE INVENTION

Figure 1:
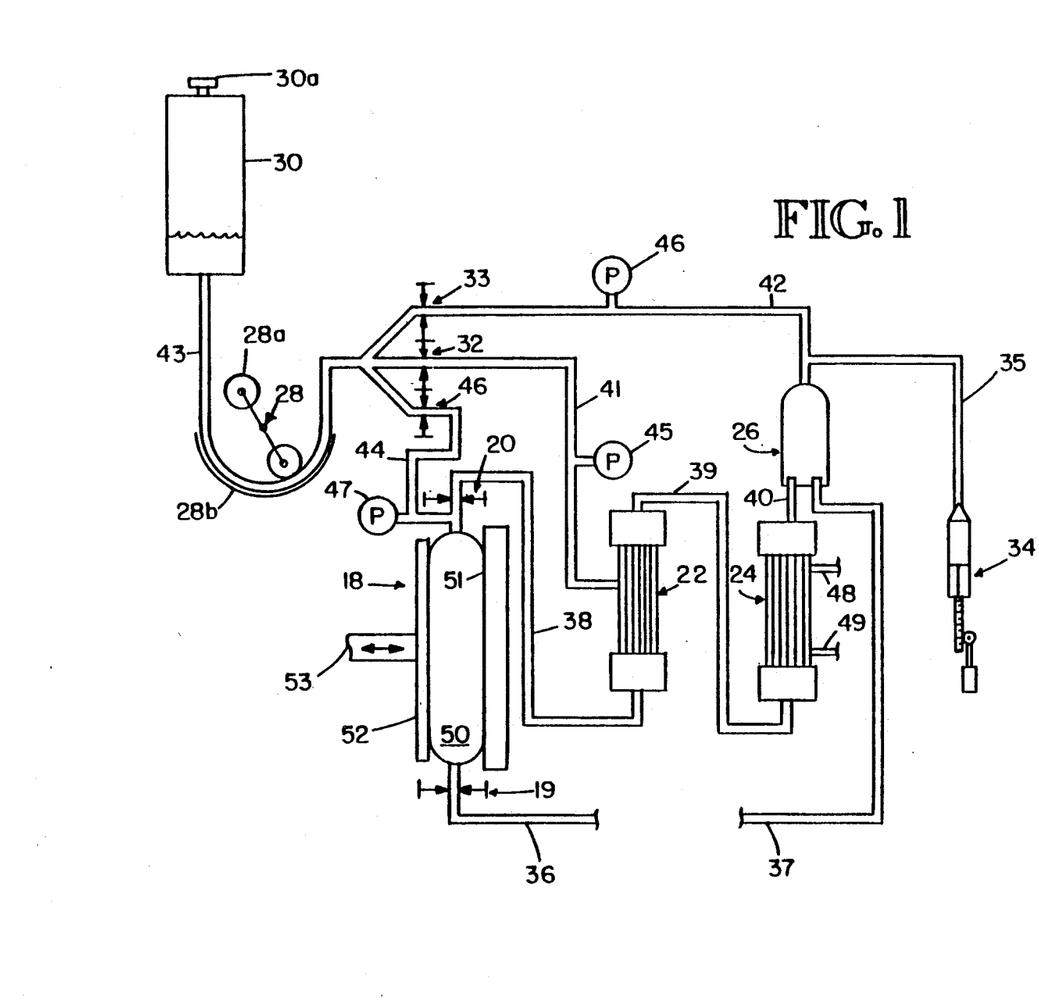
FIG. 1 is a schematic of a hemofiltration and hemodialysis system embodying the present invention.

In accordance with the present invention a blood circuit which includes a supply-regulated reversible pump 18 with ingress and egress pinch valves 19-20, the blood side of a hemofilter 22, a hemodialyzer 24, and an air-collection chamber 26 arranged in series, interacts in a closed system with a filtrate circuit comprising the filtrate side of the hemofilter 22, a reversible roller pump 28, a reservoir 30, and pinch valves 32, 33. A suitable anticoagulant such as heparin is introduced and metered to the blood circuit by a syringe pump 34 via a tube 35 which preferably discharges to the air-collection chamber 26.

When a patient is expected to be on dialysis for an extended period of time it is common to surgically create for ease of blood access an enlarged vein in one of the patient's limbs. In preparation for a dialysis treatment, two needles are inserted a few centimeters apart into the blood access. The upstream needle is connected to a flexible tube 36 (hereinafter called the "arterial tube") leading to the pump 18, and the downstream needle is connected to a flexible tube 37 (hereinafter called the "venous tube") returning to the patient from the air-collection chamber 26. In some instances a single needle is used, in which case the arterial and venous tubes 36, 37 are both connected to the needle via a T-fitting.

The tubes 36, 37 are part of the blood circuit together with a flexible tube 38 between the pump 18 and hemofilter 22, tube 39 between the hemofilter 22 and dialyzer 24, and tube 40 connecting the dialyzer to the air-collection chamber 26. The tubing in the filtrate system comprises a flexible tube 41 connected to the filtrate side of the hemofilter 22, a flexible tube 42 connected to the top of the air-collection chamber 26, and a flexible tube 43 leading from the bottom of the reservoir 30 to a Y-connection with the tubes 41, 42. The reservoir 30 may comprise a vessel with a filtered air vent or a collapsible air-tight bag. It is also preferred to provide a tube 44 extending from the pump end of the tube 38 to a connection with the tube 43 and to equip the tube 44 with a pinch valve 46. The tubes 41, 42, and 44 preferably have branches containing pressure sensors 45-47, respectively, for pressure monitoring. The 30 dialysate side of the dialyzer 24 has supply and discharge ports 48, 49 connected to a dialysate supply and to a drain.

Figures 3, 4:
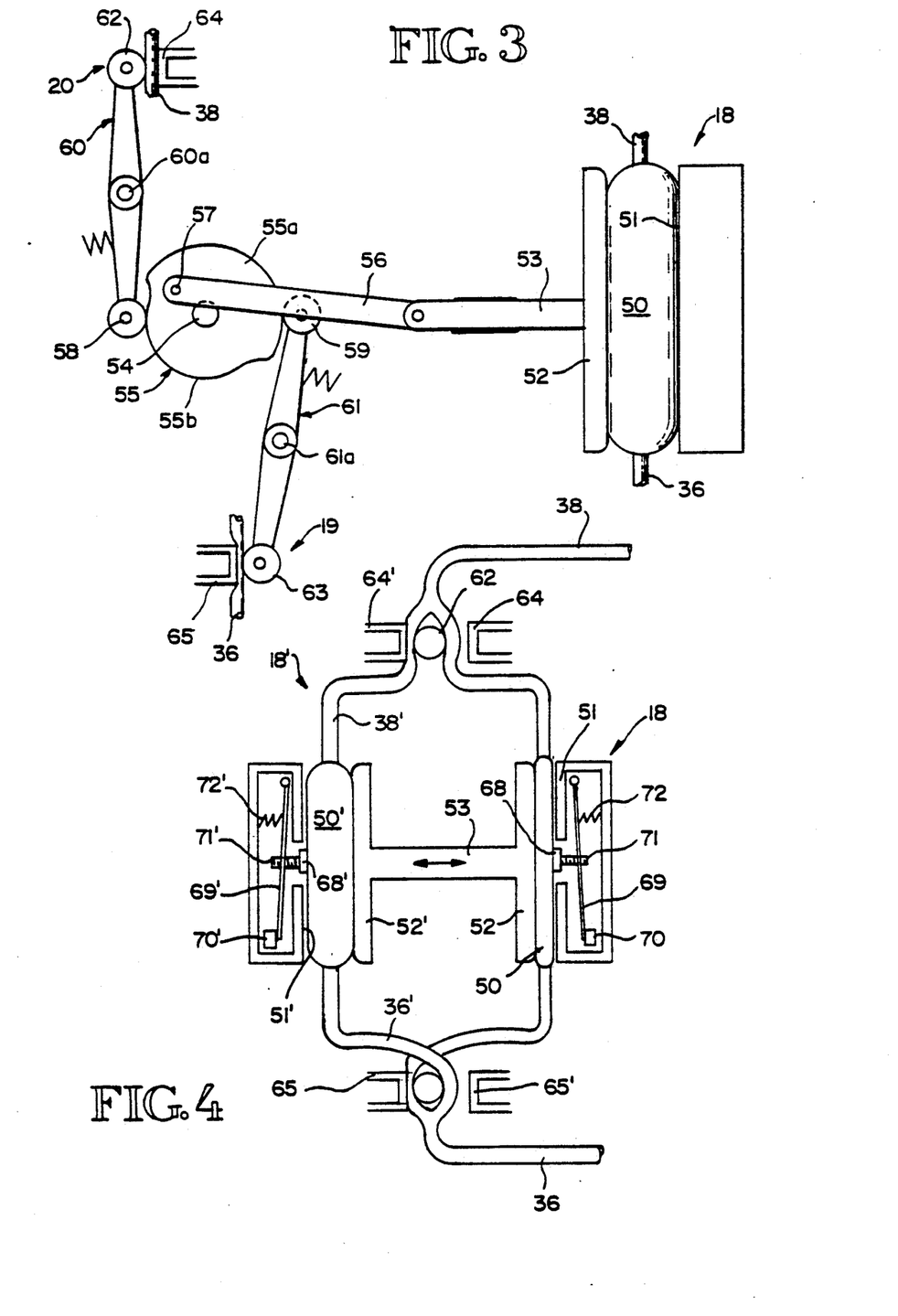
FIG. 3 is a layout of the pumping portion of the system when a single pumping chamber is used, and showing the condition when the chamber is slightly compressed.
FIG. 4 is a layout showing use of a two-chamber pumping arrangement in the system, and illustrating the condition when one chamber is nearly fully compressed and the other chamber is nearly fully expanded.

Directing attention to FIG. 3, the blood pump 18 has an elongated squeeze chamber 50 functioning between pinch valves 19-20 acting on the arterial tube 36 and on the egress tube 38 leading to the hemofilter 22. The squeeze chamber 50 is located between a stationary wall 51 and a reciprocating compression shoe 52. The shoe 52 is mounted on a slide rod 53 which is slowly driven back and forth by a driven shaft 54 via a combination crank and cam member 55 and a connecting link 56 which is pivotally connected at its ends by pins 57 to member 55 and slide rod 53. A reversible motor with a gear reduction unit (not shown) may be used to drive the shaft 54.

The member 55 has a lifting lobe 55a which encompasses about 190 degrees and a return section 55b. Riding on the periphery of member 55 are two diametrically opposite cam followers 58, 59 mounted on the ends of rockers 60, 61. These are centrally pivotally mounted at 60a, 61a and are spring loaded to swing the cam followers into constant engagement with member 55. On their ends opposite from the cam followers 58, 59 the rockers 60, 61 carry round pinch elements 62, 63 which oppose stationary blocks 64, 65. The pinch element 63 and block 65 comprise the ingress valve 19, and the pinch element 63 and block 64 comprise the egress valve 20. The arterial ingress tube 36 passes between the pinch element 63 and the block 65, and the egress tube 38 passes between the pinch element 62 and the block 64. When the cam followers 58, 59 are lifted radially away from the shaft 54 by the lobe 55a as the shaft 54 turns clockwise, for example, the pinch elements 62, 63 are urged toward the blocks 64, 65 and cooperate therewith to respectively pinch the tubes 38, 36 to a closed position. When the cam followers 58, 59 return to engagement with the return section 55b, the pinch elements 62, 63 are moved out of tube pinching position, thereby opening tubes 38 and 36, respectively.

The stationary wall 51 is interrupted to expose a projecting button 68 extending from a swing arm 69 which is arranged to engage a microswitch 70 when the swing arm 69 is swung away from the compression chamber 50 responsive to engagement of the button 68 by the opposing wall of the chamber 50. The button 68 is preferably connected to the swing arm 69 by an adjusting screw 71 so that the extent of engagement of the chamber wall necessary to operate the microswitch 70 can be readily adjusted. A spring 72 biases the swing arm 69 toward the chamber 50. The microswitch 70 is wired in series with the motor driving the shaft 54 so that the motor operates only when the microswitch is closed.

As will later be discussed, normally at the start of a dialysis treatment with the present invention, the system will be filled with sterile dialysate which is not harmful to the patient if introduced to the patient. As previously indicated, the patient is commonly connected to the arterial and venous tubes 36, 37 via needles inserted through the wall of a blood access vein. Dialysis is normally commenced with the ingress valve 19 of the blood pump open and the egress valve 20 thereof closed. As the vessel 50 expands due to its own elasticity, it creates sufficient suction acting in conjunction with the pressure of the blood exiting the patient, to potentially fill the vessel 50.

When blood initially enters the squeeze chamber 50 from the patient, normally the microswitch 70 is open and the motor driven shaft 54 is stationary. Then as the chamber 50 expands and begins to fill with blood; it firmly engages the compression shoe 52, wall 51, and button 68. The microswitch 70 is responsively closed, thereby starting the motor to drive shaft 54 so that expansion of the chamber 50 can continue as entry flow of the blood from the patient continues. If the shaft 54 turns so rapidly that the slide rod 53 moves away from the stationary wall 51 at a rate faster than the expansion rate of the squeeze chamber 50, the microswitch 70 will open, thereby stopping the motor until the expansion of the chamber 50 catches up to the then position of the compression shoe 52. Thus the blood pump 18 is regulated by the supply of blood from the patient. Filling of the chamber 50 continues until the cam follower 59 begins to climb down from the lobe 55a to close the ingress valve 19 and, the cam follower 58 reaches the lobe 55a to open the egress valve 20 after the ingress valve is closed. By this time, the connecting link 56 has begun to reverse its stroke to commence compression of the chamber 50 and the start of a pumping cycle. Compression continues until the start of another chamber filling cycle.

When the egress valve 20 opens at the start of a pumping cycle, and blood is forced from the vessel 50 by the compressing action of the shoe 52, the pinch valve 32 in the filtrate circuit is opened and the filtrate pump 28 is started so that when the pumped blood passes through the hemofilter 22, filtrate from the blood will be pumped from the hemofilter to the reservoir 30 via tubes 41 and 43. The circulating blood then passes through tube 39 to the dialyzer 24 for treatment by a suitable dialysate passing on the outside of the multitude of tubular membranes within which the blood is passing. The blood flows from the dialyzer into the air collection chamber 26 where it is treated with an anticoagulant fed by syringe pump 34. This pump may have its plunger connected to a slide-mounted rack operated by a pinion rotated by a stepper motor. Treated blood returns to the patient from the chamber 26 through the venous tube 37.

While the blood initially passes through the blood circuit at the start of the treatment, it displaces the dialysate in the blood circuit, and the displaced dialysate passes through the venous tube 37 into the patient. When the reservoir 30 is filled a predetermined amount corresponding to the increased liquid retention of the patient since the last dialysis treatment, the filtrate pump 28 is stopped and the pinch valve 32 is closed. If the patient shows signs of discomfort or distress because of a liquid shortage caused by the treatment, the filtrate pump 28 is started in reverse with the pinch valve 33 open so that filtrate can be reintroduced to the patient via the tube 42, air collection chamber 26, and venous tube 37 where it blends with the returning blood to the patient.

After a dialysis treatment is completed it is necessary to clean all of the system components to be reused. Then the system is sterilized with a suitable sterilant solution which is left in the system until the system is to be again activated for another treatment. At that time the sterilant is replaced by dialysate before the system is connected to the patient.

One of the advantages of the system is that the vessel 50 and related ingress and egress blood tubes 36, 38 can be removed laterally as a unit from the blood pump and pinch valve mechanisms in the blood circuit, and that the filtering tube 43 can be removed laterally from the roller pump 28 in the filtrate circuit without being disconnected. Specifically, vessel 50 can be removed from between the compression shoe 52 and wall 51; tubes 36 and 38 can be removed from between pinch elements 62, 63 and blocks 64, 65; the tubes 41, 42 and 44 can be removed from the pinch valves 45, 46 and 47; and the filtrate tube 43 can be removed from between the roller elements 28a and arcuate abutment plate 28b of the roller pump 28. Thus, all of the system subjected to contact with a patient's blood or filtrate during dialysis, including all tubes, valves, pressure monitors, the reservoir 30, hemofilter 22, dialyzer 24, air collection unit 26, and anticoagulant pump 34, can be removed as a module from the dialysis machine for storage to be used for subsequent dialysis treatments of the same patient. Furthermore, this module can be cleaned, tested, and sterilized on a processing machine, thereby freeing the dialysis machine for use on another patient after inserting of that patient's module. This processing machine preferably includes reversible pumps and pinch valve mechanisms arranged to function on the vessel 50, blood tubes 36, 38 and filtrate tubes 41, 42, and 43 by a squeezing action in a suitable manner like the blood pump 18 and its related pinch valves 19-20, and filtrate pump 28 and pinch valves 32, 33 and 46.

Since post-treatment operations on the system will be basically the same whether or not performed on another machine, the following example will be with reference to the machine previously described.

After dialysis is complete and the blood in the blood circuit has been returned to the patient and tubes 36, 37 have been disconnected from the patient, it is preferred to connect them to a valve block 74 (FIG. 2) having four ports, one for the arterial tube 36, a second for the venous tube 37, a third for a drain tube 75, and a fourth for an infeed tube 76. The block 58 contains a cross-over valve 78 for connecting the tubes 36, 37 and respective valves 79, 80 for controlling flow through the drain and infeed tubes 75, 76.

Figure 2:
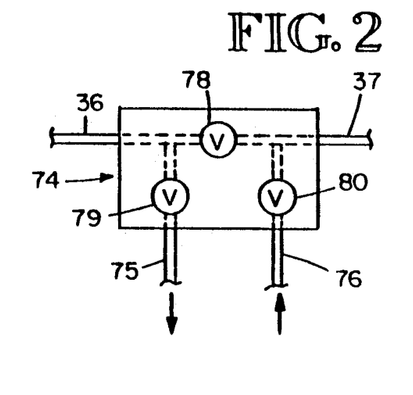
FIG. 2 is a schematic of a valve block for use during post-treatment operations on the system.

To clean blood residue from the system it is necessary to flush and back-wash the components several times with a suitable flushing solution which will pass through the pores in the multitude of tubular membranes in the filter 22 and dialyzer 24. The flushing solution is preferably introduced to the system through the dialysate infeed port 48 of the dialyzer 24 and the infeed tube 76 to the block 74.

The system can initially be drained by opening the drain valve 79 and cross-over valve 78, and reversing the filtrate pump 28 and blood pump 18 for down-flow with the pinch valves 32, 33 and 46 open. Then the system can be filled with a suitable cleaning solution such as a weak household bleach through the infeed tube 76 with valve 79 closed and the filtrate pump 28 and blood pump 20 reversed for up-flow. The hemodialyzer 24 can be back-washed by introducing cleaning solution through the dialysate intake 48. Repeatedly draining and filling of the system with the cleaning solution and then with filtered water cleans out all blood and blood filtrate residue from the system components. Then the system is filled with a suitable sterilant such as formaldehyde.

When the system is to be used again, the sterilant is removed from the system, preferably by dialysis. Dialysate is circulated through the dialyzer 24 with the arterial and venous tubes 36, 37 connected together via valve 78 with valves 79, 80 being closed, and the blood pump 18 operating in up-flow mode. The filtrate pump 28 is operated in the up-flow direction with the pinch valves 32, 33 and 46 open to fill the reservoir 30, and then is reversed. This sequence is repeated until all of the sterilant has been purged from the system through the dialyzer membrane and dialysate discharge port 49. During the procedure the anticoagulant pump 34 is operated a sufficient time to remove sterilant from the connecting tube between the pump 34 and the air collection chamber 26. When the sterilant has been removed by dialysis in preparation for patient treatment, the system contains sterile dialysate.

It is preferred to test the integrity and permeability of the hemofilter and hemodialyzer membranes between dialysis treatments, normally before the sterilant is added. For membrane leakage testing, the reservoir 30 is emptied and the blood pump 18 is run forward at approximately 200 ml/min. Simultaneously, the filtrate pump 28 is run in reverse to draw air through the empty filtrate reservoir 30 and pump it through tube 41, with valve 32 open, into the jacket of hemofilter 22 until the pressure reaches a prescribed limit (e.g., 250 mmHg).

Both pumps 18, 28 are then stopped and pressure decay is monitored for approximately 4 minutes. Next, air from the reservoir 30 is pumped through valve 33 into the blood circuit via tube 42 and air collection chamber 26 until pressured to a similar level monitored by sensor 46. If pressure decay read at sensor 45 or 40 exceeds limits appropriate to the hemofilter and hemodialyzer being used, the system will be in a failure condition. This membrane leakage test is based on the fact that air will pass through a small defect more rapidly than a liquid, and therefore is a more sensitive indicator of membrane integrity.

The present invention measures membrane permeability in the hemodialyzer 24 by filling the blood lines with filtrate to a preselected pressure, and then monitoring the pumping rate required to maintain that pressure. This is accomplished by activating the filtrate pump 28 in reverse, thereby causing filtrate to pass from the filtrate reservoir 30 through valve 33 and tube 42 into the blood circuit via the air collection chamber 26. Filling continues until a predetermined pressure (for example, 250 mmHg) is reached. During the fill, some fluid will have passed across the hemofilter membrane, equalizing the pressure between the hemofilter 22 and the tube 41 to valve 32. At this point, fluid can only leave the blood circuit by passing across the hemodialyzer membrane to the dialysate side; the faster the rate, the greater the permeability. After pressurization, the pumping rate of the filtrate pump 28 required to maintain this pressure is monitored. If this rate is below the desired threshold value for the particular hemodialyzer model, membrane permeability is inadequate.

A similar test may be applied to the hemofilter 22 by opening valve 32 and pressurizing the hemofilter jacket, with filtration occurring from the jacket to the blood side of the hemofilter. A pumping rate below the ordinary threshold indicates excessive membrane blockage. It should be noted that the hemofilter and hemodialyzer tests also may be performed by pressurizing the system as described herein, then stopping the filtrate pump 28 and monitoring the rate of pressure decay as the indication of membrane permeability of the hemodialyzer 24 and the hemofilter 22.

The invention has been described with respect to a single blood pump 18. However, as shown in FIG. 4, the blood pump mechanisms is ideal for operating two blood pumps 18, 18' in alternating cycles. In the two-pump arrangement the slide rod 53 i connected to a second compression shoe 52' operating with a second squeeze chamber 50'. This second chamber connects at its ends with ingress and egress tube branches 36', 38' which pass between the pinch elements 62, 63 and a second set of stationary blocks 64', 65'. A second microswitch 70' is operated in response to expansion of the chamber 50' against a wall 51' and second button 68' by way of an adjustment screw 71' and swing arm 69' which is biased by a spring 72'.

By the described two-pump system while one of the chambers 50, 50' is being compressed to discharge blood, the other chamber is being filled from the patient. Feedback from one squeeze chamber to the other is prevented by the fact that the squeeze elements 62, 63 alternatively pinch the ingress and egress tubes for the chambers. The electrical circuit from the blood pump motor to the switches 70, 70' is such that the motor can only be activated by alternate filling of the squeeze chambers 50, 50'.

The pressure sensor 47 makes it possible to monitor the output pressure of the blood pump(s), and the pressure sensors 45, 46 enable pressure monitoring of the filtrate circuit. It will be appreciated that the described system can be controlled by an automated electrical control system connected to the motor for the blood pump(s) and filtrate pump 28, and to solenoids operating the pinch elements of the valves 32, 33 and 46. It will also be appreciated that the ingress and egress pinch valves 19, 20 can have their pinch elements 62, 63 solenoid operated, and that other mechanisms can be used to operate the compression shoes 52, 52'.

We claim:

1. A hemodialysis system comprising:
   a blood pump having a blood outlet and a blood inlet for connection to a patient via an arterial route;
   a hemofilter having a blood inlet connected to said blood outlet of the pump, and having a blood outlet and a filtrate outlet;
   a hemodialyzer having a blood outlet, a blood inlet connected to said blood outlet of the hemofilter, and a dialysate inlet and outlet;
   a filtrate reservoir;
   an air-removal and filtrate pump having an outlet connected to said reservoir and having an inlet;
   an air collection chamber having a blood inlet connected to said blood outlet of the hemodialyzer, a blood outlet for connection to a patient via a venous route, and an air removal outlet;
   tube and valve means selectively connecting and disconnecting said inlet of the air-removal and filtrate pump with said filtrate outlet of the hemofilter and air removal outlets; and means for introducing an anti-coagulant to said air collection chamber.

2. A hemodialysis system according to claim 1 in which additional tube and valve means selectively connect said blood outlet of said blood pump with said reservoir.

3. A blood pumping system for a hemodialysis circuit comprising:
   a flexible vessel connected to flexible ingress and egress tubes for entry and discharge of blood from a patient, said vessel and tubes being adapted to self return to their original shapes when released after being collapsed;
   ingress and egress pinch valve mechanisms arranged for selectively collapsing said ingress and egress tubes, respectively;
   compression means for selectively collapsing said vessel during a compression stroke to discharge blood into said egress tube when said egress tube is open and said ingress tube is collapsed, said compression means also having a return stroke permitting said vessel to return to its original shape to create a suction in said ingress tube when said egress tube is collapsed and said ingress tube is open; and
   control means operatively connected to said valve mechanisms and compression means for operating in a cycle wherein said ingress tube is open and said egress tube is closed during said return stroke, wherein said ingress tube is closed and said egress tube is open during said compression stroke, and wherein, said ingress tube is closed before said egress tube is opened at the start of said compression stroke.

4. A hemodialysis method comprising:
   circulating a patient's blood from and back to the patient in a closed primary blood circuit through a hemofilter, hemodialyzer, and air extraction chamber arranged in series;

collecting filtrate from the hemofilter in a reservoir located in a closed secondary circuit connected to said primary circuit; and pumping air from said air extraction chamber to said reservoir through said secondary circuit to remove all air from the circulating blood before return to the patient.

5. A hemodialysis method according to claim 4 in which collected filtrate is returned to said circuit.

6. A hemodialysis method according to claim 4 in which collected filtrate is returned to the circuit via the air collection chamber.

7. A hemodialysis method according to claim 4 in which an anti-coagulant is introduced to said air collection chamber to prevent blood coagulation in said circuit.

8. A hemodialysis method comprising:

introducing blood from a patient into an external blood circuit connected to the patient;

isolating equal volumetric increments of the introduced blood in a flexible vessel in said external circuit;

linearly compressing said vessel each time only that it contains one of said increments, and advancing the respective increment along said external circuit while the vessel is being compressed;

filtering the advancing increments and thereby removing excess fluid as filtrate; and diffusing solutes from each increment as its advances further along said external circuit for return to the patient.

9. A hemodialysis method according to claim 8 in which said filtering of the advancing increments of blood comprises removing and storing excess fluid from the blood, and returning some of said stored excess fluid to said external circuit from time to time to control the fluid content of the blood.

10. A method according to claim 8 in which said filtrate is collected in a filtrate circuit, and in which some of said filtrate is returned from said filtrate circuit to said external circuit when dialysis has been completed to displace the blood remaining in said external circuit and thereby return such blood to the patient.

11. A hemodialysis method comprising:

circulating blood during a treatment period from a patient through an external circuit and back to the patient;

filtering excess fluid from the circulating blood and collecting the excess fluid filtrate;

diffusing urea from the circulating blood; and displacing the blood remaining in said external circuit at the close of said treatment period with the collected filtrate to return such blood to the patient.

12. A hemodialysis method comprising:

circulating blood during a treatment period from a patient through an external circuit and back to the patient;

filtering excess fluid from the circulating blood by a hemofilter in said external circuit and collecting the excess fluid filtrate in a filtrate reservoir within a filtrate circuit in a sterile environment;

dialyzing the circulating blood at a dialyzer in said external circuit; and displacing the blood remaining in said external blood circuit at the close of said treatment period with the collected excess fluid filtrate to return such remaining blood to the patient.

13. A method according to claim 12 including the following additional steps:

disconnecting the external circuit from the patient and closing the external circuit;

introducing a cleaning agent on the dialysate side of said dialyzer; and passing said cleaning agent through the dialyzer membrane into said external circuit.

14. A method according to claim 13 including the following additional steps:

removing said cleaning agent and introducing a sterilant to said external circuit; and removing said sterilant in preparation for a dialysis treatment by dialysis of the sterilant through said dialyzer membrane.

15. A hemodialysis system comprising:

a hemodialyzer;

a flexible vessel adapted to self-expand to its original shape after being deformed by compression;

a closed blood circuit for passing blood from a patient to said vessel and from said vessel to the hemodialyzer, and for returning blood from the hemodialyzer to the patient, said blood circuit having an ingress valve between said vessel and the patient, and an egress valve between said vessel and the hemodialyzer;

apparatus for alternately compressing and releasing said vessel in alternating compression and release strokes; and control means for starting each compression stroke after a predetermined operation of said vessel responsive to flow of blood from the patient in accordance with the patient's own blood delivery rate, and for controlling the start of each release stroke, said control means being operatively associated with said valves for opening said ingress valve and closing said egress valve preliminary to the start of each release stroke, and for closing the ingress valve and opening the egress valve preliminary to the start of each compression stroke.

16. A system according to claim 15 in which said control means includes a sensor normally contacting said vessel and adapted to deactivate said apparatus during said release stroke whenever the release stroke progresses beyond the expansion of the vessel.

17. A hemodialysis system comprising;

a hemodialyzer;

a blood flow circuit for connection to a patient including a flexible vessel and flexible input and output tubes leading to said vessel from the patient and leading from the vessel to said hemodialyzer, said vessel and tubes having a self return characteristic when collapsed; and squeeze means external to said tubes and external to said vessel for selectively collapsing them in a pumping cycle wherein said vessel collapses in a pumping stroke and expands in a suction stroke, wherein a portion of said input tube is collapsed as an input valve prior to the start of said pumping stroke and is released for expansion at the beginning of said suction stroke, and wherein a portion of said output tube is collapsed as an output valve at the beginning of said suction stroke and is released for expansion at the beginning of said pumping stroke; and control means for activating said squeeze means to start said pumping stroke only when said vessel contains a preset volume of blood.

18. A blood pumping system comprising:
a blood pumping system for a hemodialysis circuit comprising:
a flexible vessel connected to flexible ingress and egress tubes for entry and discharge of blood from a patient, said vessel and tubes being adapted to self return to their original shapes when released after being collapsed;
ingress and egress pinch valve mechanisms arranged for selectively collapsing said ingress and egress tubes, respectively;
compression means including a rotary combination crank and cam member, a compression shoe engaging said vessel, and a link pivotally connected to said member and shoe for linearly reciprocating said shoe responsive to turning of said crank and cam member to alternately move said shoe in a vessel compressing stroke and a vessel expansion stroke; and
pinch valve mechanisms including rockers with pinch elements at one end of the rockers and cam followers at the other end thereof engaging said crank and cam member while it turns to responsively pinch and release portions of said tubes by said pinch elements in a cycle wherein said ingress tube is open and said egress tube is closed during said expansion stroke and wherein said ingress tube is closed and said egress tube is open during said compression stroke.

19. A hemodialysis system comprising:
a hemofilter having a membrane with a blood side and a filtrate side;
a hemodialyzer having a membrane with a blood side and a dialysate side;
an air removal station;
a reservoir connected by a filtrate circuit to said filtrate side of the hemofilter and to the top of said station;
pump means for circulating blood in a blood circuit from a patient to said blood sides and back to the patient via said station; and
circulating means for circulating air through said filtrate circuit to said reservoir from the circulating blood in said blood circuit at said station, and for circulating filtrate to said reservoir through said filtrate circuit.

20. A hemodialysis system according to claim 19 in which anti-coagulant introducing means is connected to said station.

21. A hemodialysis system according to claim 19 in which said circulating means comprises a reversible pump, a pinch valve between said pump and said hemofilter, and a pinch valve between said pump and said station, whereby filtrate can be pumped from said hemofilter to said reservoir, or filtrate can be pumped from said reservoir to said blood circuit at said station or to said blood circuit at said hemofilter via the membrane of the hemofilter.

22. A hemodialysis system according to claim 21 in which said circulating means includes a reversible pump, and said filtrate circuit also connects with said blood circuit at the outlet side of said pump means by a branch having a pinch valve and a pressure sensor located between said pinch valve and said pump means.

23. A hemodialysis system comprising:
a blood pump having a blood outlet and a blood inlet for connection to a patient via an arterial route;
a hemofilter having a blood inlet connected to said blood outlet of the pump, and having a blood outlet and a filtrate outlet;
a hemodialyzer having a blood outlet, a blood inlet connected to said blood outlet of the hemofilter, and a dialysate inlet and outlet;
a filtrate reservoir;
an air-removal and filtrate pump having an outlet connected to said reservoir and having an inlet;
an air extraction chamber having a blood inlet connected to said blood outlet of the hemodialyzer, a blood outlet for connection to a patient via a venous route, and an air removal outlet;
tube and valve means selectively connecting and disconnecting said inlet of the air-removal and filtrate pump with said filtrate outlet of the hemofilter and air removal outlets; and
means for introducing an anti-coagulant to said air extraction chamber;
said pumps being selectively reversible to pump filtrate from said reservoir to the hemofilter and/or air extraction chamber to enable return of the blood in the system to the patient via the arterial and venous routes at the close of a hemodialysis treatment.

24. A hemodialysis method comprising:
circulating a patient's blood from and back tot he patient in a circuit through a hemofilter, hemodialyzer, and air extraction chamber arranged in series;
collecting filtrate from the hemofilter in a reservoir;
extracting air from said air extracting chamber and collecting it in said reservoir to remove air from the circulating blood before return to the patient;
and returning some of the collected filtrate from the reservoir to the circuit at the close of dialysis such as to return the patient's blood in the circuit to the patient.

25. A hemodialysis method comprising:
introducing blood from a patient into an external blood circuit connected to the patient;
isolating volumetric increments of the introduced blood in a flexible vessel in said external circuit;
linearly compressing said vessel each time only that it contains one of said increments, and advancing the respective increment along said external circuit while the vessel is being compressed;
filtering the advancing increments and thereby removing excess fluid as filtrate;
collecting said filtrate in a filtrate circuit;
diffusing solutes from each increment as its advances further along said external circuit for return to the patient; and
returning some of said filtrate from said filtrate circuit to said external circuit when dialysis has been completed to displace the blood remaining in said external circuit and thereby return such blood to the patient.

26. A hemodialysis system comprising:
a blood circuit;
a filtrate circuit connected to said blood circuit;
means for introducing blood from a patient into said blood circuit and for returning blood from said blood circuit to the patient;

means for isolating equal volumetric increments of the introduced blood in a flexible vessel in said blood circuit;

means for compressing said vessel each time, and only each time, that it contains one of said increments so that the respective increment is advanced along said blood circuit;

filtering means for filtering the advancing increments to remove excess fluid as filtrate;

means for collecting said filtrate in said filtrate circuit;

means for selectively returning some of said filtrate from said filtrate circuit to said blood circuit for selectively controlling the amount of fluid in the blood returned to the patient.

27. A hemodialysis system according to claim 26 in which means are provided for diffusing solutes from each said increment as it advances along said blood circuit from said filtering means for return to the patient.

28. A hemodialysis system comprising:

a blood circuit;

a filtrate circuit connected to said blood circuit;

means for introducing blood from a patient into said blood circuit;

means for isolating equal volumetric increments of the introduced blood in a flexible vessel in said blood circuit;

means for linearly compressing said vessel each time, and only each time, that it contains one of said increments, and advancing the respective increment along said blood circuit while the vessel is being compressed;

means for filtering the advancing increments to remove excess fluid as filtrate;

means for collecting said filtrate in said filtrate circuit;

means for diffusing solutes from each increment as it advances further along said blood circuit for return to the patient; and means for selectively returning some of said filtrate from said filtrate circuit to said blood circuit.

* * * * *

UNITED STATES PATENT AND TRADEMARK OFFICE
CERTIFICATE OF CORRECTION

PATENT NO.   :   5,114,580

DATED        :   May 19, 1992

INVENTOR(S)  :   Suhail Ahmad et al

It is certified that error appears in the above-identified patent and that said Letters Patent is hereby corrected as shown below:

Col. 10, claim 15, line 33, delete "operation" and
   substitute therefor -- expansion --.

In column 12, claim 24, line 30, please delete "tot he" and
   substitute therefor -- to the --.

In column 12, claim 25, line 47, please delete "only".

Signed and Sealed this

Twenty-fourth Day of August, 1993

Attest:

BRUCE LEHMAN

*Attesting Officer*     Commissioner of Patents and Trademarks